United States Patent
Fahey et al.

(10) Patent No.: US 12,419,782 B2
(45) Date of Patent: Sep. 23, 2025

(54) APPARATUS AND METHODS FOR IMPROVED NASAL CAVITY TREATMENTS

(71) Applicant: Arrinex, Inc., Redwood City, CA (US)

(72) Inventors: Brian Fahey, Menlo Park, CA (US); William Jason Fox, San Mateo, CA (US)

(73) Assignee: Arrinex, Inc., Redwood City, CA (US)

( * ) Notice: Subject to any disclaimer, the term of this patent is extended or adjusted under 35 U.S.C. 154(b) by 703 days.

(21) Appl. No.: 17/638,541

(22) PCT Filed: Sep. 17, 2020

(86) PCT No.: PCT/US2020/051177
§ 371 (c)(1),
(2) Date: Feb. 25, 2022

(87) PCT Pub. No.: WO2021/055544
PCT Pub. Date: Mar. 25, 2021

(65) Prior Publication Data
US 2022/0313484 A1 Oct. 6, 2022

Related U.S. Application Data

(60) Provisional application No. 62/901,656, filed on Sep. 17, 2019.

(51) Int. Cl.
*A61F 7/12* (2006.01)
*A61B 18/02* (2006.01)
*A61F 7/00* (2006.01)

(52) U.S. Cl.
CPC .............. *A61F 7/123* (2013.01); *A61B 18/02* (2013.01); *A61F 2007/0006* (2013.01); *A61F 2007/0056* (2013.01); *A61F 2007/126* (2013.01)

(58) Field of Classification Search
CPC ........................ A61B 18/02; A61B 2018/0231
See application file for complete search history.

(56) References Cited

U.S. PATENT DOCUMENTS

| | | |
|---|---|---|
| 2016/0354135 A1 | 12/2016 | Saadat |
| 2018/0125560 A1 | 5/2018 | Saadat et al. |
| 2019/0201069 A1 | 7/2019 | Wolf et al. |

OTHER PUBLICATIONS

Dong Z. [Anterior ethmoidal electrocoagulation in the treatment of vasomotor rhinitis]. Zhonghua Er Bi Yan Hou Ke Za Zhi. 1991;26(6):358-9, 383. Chinese. PMID: 1811691. (Year: 1991).*
International Search Report mailed on Nov. 27, 2020, issued in connection with International Application No. PCT/US2020/051177, filed on Sep. 17, 2020, 6 pages.
Written Opinion mailed on Nov. 27, 2020, issued in connection with International Application No. PCT/US2020/051177, filed on Sep. 17, 2020, 11 pages.
Communication pursuant to Article 94(3) EPC issued by the European Patent Office in application No. 20 781 269.4 dated Feb. 7, 2025.

* cited by examiner

*Primary Examiner* — Kaitlyn E Smith
(74) *Attorney, Agent, or Firm* — McDonnell Boehnen Hulbert & Berghoff LLP

(57) ABSTRACT

In an example, a cryotherapy device includes an elongated shaft, and a cryotherapy delivery member coupled to a distal end of the elongated shaft. The cryotherapy delivery member is configured to apply, from a fixed position in a nasal cavity, thermal energy to at least one of a plurality of nerves in the nasal cavity or a plurality of branches of a nerve in the nasal cavity.

12 Claims, 11 Drawing Sheets

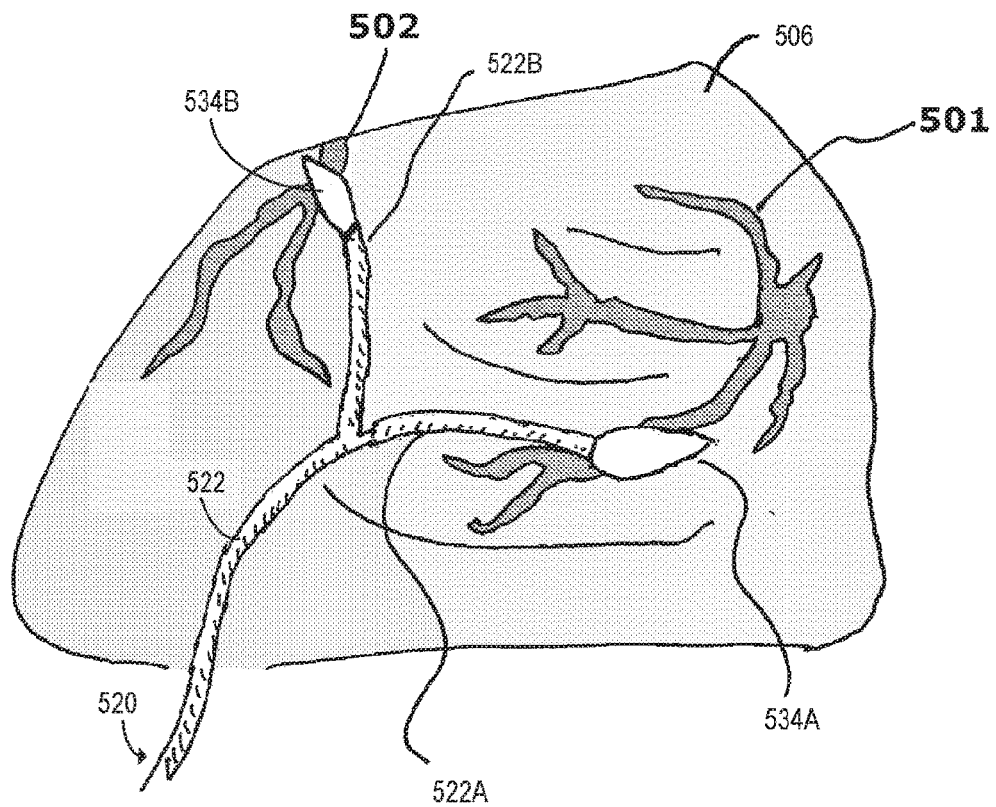
Fig. 5
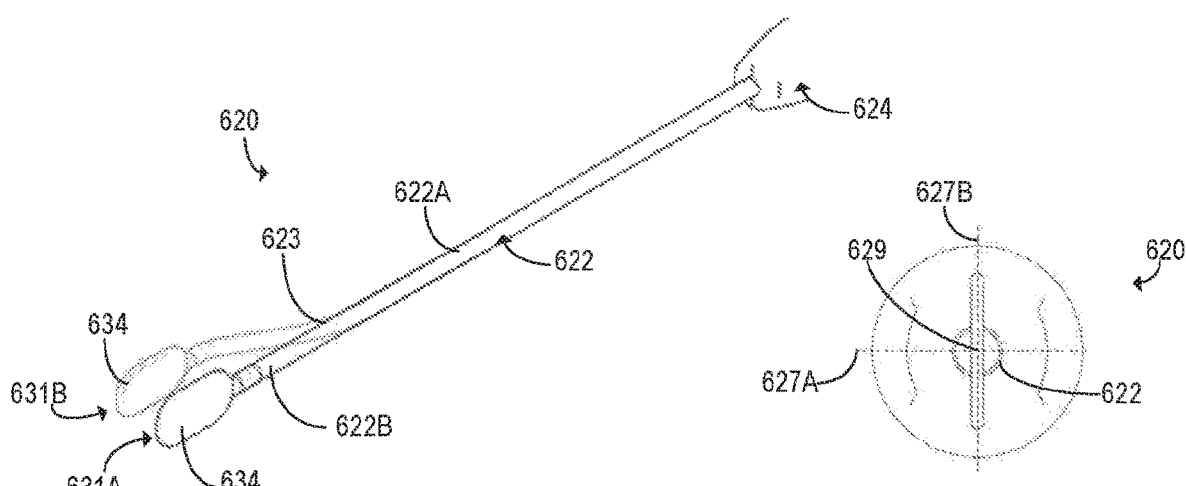
Fig. 6A
Fig 6B

APPARATUS AND METHODS FOR IMPROVED NASAL CAVITY TREATMENTS

CROSS-REFERENCE TO RELATED APPLICATION

The present application is the US national phase under 35 U.S.C. § 371 of International Application No. PCT/US2020/051177, filed Sep. 17, 2020, which claims the benefit of U.S. Provisional Patent Application No. 62/901,656, filed on Sep. 17, 2019, the contents of which are hereby incorporated by reference in their entirety.

FIELD

The present disclosure is related to the field of therapeutic thermal interventions intended for delivery within a nasal cavity and, more particularly, to apparatuses and methods for hypothermic treatments (e.g., cryotherapies including hypothermic cooling and cryoablation) delivered within the nasal cavity.

BACKGROUND

Many modern therapies involve treatments that are delivered within the nose and, in particular, within the nasal cavity. These therapies may be intended to target symptoms of sinusitis, rhinitis, nasal valve collapse, turbinate hypertrophy, and other pathologies.

Example bony structures of a nose are shown in FIG. 1A. The nose includes an external portion positioned on the face and an internal nasal cavity, which extends posteriorly. The nose is involved with creating the sensation of smell and filters, warms, and moistens air during inspiration. The external nose presents a root (or bridge), a dorsum, and a free tip or apex. The two inferior openings are the nostrils (sometimes referred to as the nares), which are bounded laterally by the ala and medially by the nasal septum. The nostrils represent the exterior entrance to the nasal cavity. The superior part of the nose is supported by the nasal bone 155, frontal bone, and maxillary bone 156; the inferior part includes a number of cartilages such as the lateral nasal cartilage 161 and the greater alar cartilage 162.

The nasal cavity extends in an antero-posterior direction from the nostrils to the choanae 193 (singular: choana) as shown in FIG. 1C. The choanae are the posterior openings of the nose. Each choana 193 is bounded medially by the vomer, inferiorly by the horizontal plate of the palatine bone 158 as shown in FIG. 1A, laterally by the medial pterygoid plate, and superiorly by the body of the sphenoid bone 159. Posteriorly, the nasal cavity communicates with the nasopharynx, which can be considered the posterior portion of the cavity. The nasal cavity is separated from the oral cavity by the hard palate.

In addition to the nostrils and choanae, the nasal cavity includes additional openings for the paranasal sinuses and the nasolacrimal duct. Further openings exist that are generally covered by mucosa (e.g., the sphenopalatine foramen 160). The nasal cavity is divided into right and left halves (each of which may also be termed a nasal cavity) by the nasal septum. Each half has a roof, floor, and medial and lateral walls. The roof of the nasal cavity is formed by nasal cartilages and several bones, chiefly the nasal bone 155 and frontal bone, the cribriform plate of the ethmoid bone 154, and the body of the sphenoid bone 159. The floor is formed by the palatine process of the maxillary bone 156 and the horizontal plate of the palatine bone 158. Thus, the floor is formed by the palate. The medial wall, or nasal septum, is formed (from anterior to posterior) by the septal cartilage, the perpendicular plate of the ethmoid bone 154, and the vomer. The lateral wall has an uneven and complicated shape, and is formed by several bones: the nasal bone 155, the maxillary bone 156, the lacrimal bone 157, the ethmoid bone 154, the inferior nasal turbinate 153, the perpendicular plate of palatine bone 158, and the medial pterygoid plate of sphenoid bone 159.

The lateral nasal wall includes three medial projections referred to as the nasal turbinates 151-153, which overlie passages known as meatuses. The inferior turbinate 153 is a separate bone, while the middle turbinate 152 and superior turbinate 151 are portions of the ethmoid bone 154. The superior meatus, under the superior turbinate 151, receives the openings of the posterior ethmoidal cells and the sphenopalatine foramen 160. The middle meatus, under the middle turbinate 152, receives the openings of the maxillary and frontal sinuses. Most anterior ethmoidal cells open proximate to the ethmoidal bulla. The inferior meatus, which lies between the inferior turbinate 153 and the palate, receives the termination of the nasolacrimal duct.

The nasal cavity is generally covered with mucosal tissue. The posterior two-thirds of the cavity include cilia, the active motion of which enable the rapid drainage of mucous backward and downward into the nasopharynx. The nasal mucosa is highly vascular, and as such it plays a significant role in warming and moistening inhaled air. The mucosa also contains large venous-like spaces known as swell bodies that may become congested during allergic reactions or infections.

The functionality of the mucosa is controlled by the nerves that innervate the nasal cavity, some of which are highlighted in FIG. 1B, which shows a view of the lateral nasal cavity wall. The nerves are responsible for sensations of touch, pressure, temperature, as well as the regulation of blood supply and the secretion of the nasal mucosa. The nerves of the nasal airway that are responsible for sensation are branches of the trigeminal nerve. The nerves that are responsible for nasal mucosa swelling and mucus secretion are nerve fibers emerging from or running proximate to the sphenopalatine ganglion 180, and are referred to as the Posterior Nasal Nerves (PNN) 176-179 and the Anterior Ethmoidal Nerve (AEN) 175.

The PNN 176-179 are generally responsible for the parasympathetic control of the nasal mucosa. In some regions of the nasal cavity, other nerves referred to as the accessary posterior nasal nerves (APNN) may additionally or alternatively innervate the mucosa. The APNN generally originate from regions proximate to the palatine canal 181, which houses the greater and lesser palatine nerves 182. Branches of the AEN 175 are responsible for the sensation of the anterior portion of the nasal airway and the exterior of the nose and middle of the face. These branches are also involved in controlling itching, sneezing, and pain sensation in this portion of the airway and face. The branches of the AEN that run along the lateral nasal wall are the external nasal branch 183, which is responsible for the sensation of the exterior portion of nose and middle portion of the face, and the lateral nasal branches 184 and internal nasal branches 185, which are responsible for sensation and parasympathetic control on the anterior side of the nasal airway. The AEN receives its parasympathetic fibers from the ciliary ganglion.

An additional view of nerves in the nasal cavity is shown in FIG. 1C, which features a view of the septal wall. One nerve of relevance is the septal branch 191 of the AEN 175.

The septal branch 191 is responsible for sensation and parasympathetic control for the anterior side of the nasal airway as well, and works in tandem with the lateral nasal branch 184 and the internal nasal branch 185. The nasopalatine nerve 192, which innervates the nasal airway mucosa proximate to the sphenopalatine foramen on the lateral wall, passes across the roof of the nasal cavity below the orifice of the sphenoidal sinus at or near the choana 193 to reach the septum. The nasopalatine nerve is responsible for sensation and parasympathetic control of the posterior side of the nasal septum.

SUMMARY

The present disclosure is related to systems, devices, and methods for improving the treatment of ailments related to nasal nerve dysfunction, including rhinitis. More specifically, the present disclosure relates to systems and methods for targeting one or more nerve locations to be treated within the nasal cavity. In examples, the treatments involve thermal treatments such as radiofrequency ablation and cryoablation. The disclosure can be particularly useful during cryotherapy procedures applied within the upper airway.

It is an objective of the present disclosure to provide methods, devices, and systems that advance the field of medicine such that patients suffering from ailments such as rhinitis achieve more substantial and longer-lasting relief from symptoms. More specifically, it is an objective of the present disclosure to provide a more complete treatment of patient conditions that arise from disorders involving the nasal nerves. Accomplishing this objective is valuable because it will improve quality of life for patients and reduce the burden on the healthcare system that arises from patients frequently returning to be retreated after relapse of symptoms.

In an example, a cryotherapy device includes an elongated shaft, and a cryotherapy delivery member coupled to a distal end of the elongated shaft. The cryotherapy delivery member is configured to apply, from a fixed position in a nasal cavity, thermal energy to at least one of a plurality of nerves in the nasal cavity or a plurality of branches of a nerve in the nasal cavity.

In another example, a cryotherapy device includes an elongated shaft comprising a proximal portion and a distal portion. The cryotherapy device also includes an articulation joint that couples the proximal portion to the distal portion of the elongated shaft. The articulation joint is configured to articulate the distal portion relative to the proximal portion. The cryotherapy device further includes a cryotherapy delivery member coupled to a distal portion of the elongated shaft, wherein the cryotherapy delivery member is configured to apply thermal energy to a target tissue.

In another example, a method for applying cryotherapy to a target tissue in a nasal cavity of a patient includes inserting a cryotherapy device into the nasal cavity of the patient. The cryotherapy device includes a cryotherapy delivery member. The method also includes positioning the cryotherapy delivery member at a position that is proximate to an anterior ethmoidal nerve (AEN). The method further includes delivering, using the cryotherapy delivery member, thermal energy to the AEN.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

FIG. 5 illustrates a cryotherapy device with multiple cryotherapy delivery elements positioned in the nasal cavity of a patient, according to an example.

FIG. 6A illustrates a first view of the distal portion of a cryotherapy device with an articulating portion, according to an example.

FIG. 6B illustrates a second view of the cryotherapy device, according to an example.

DETAILED DESCRIPTION

Figure 1A:
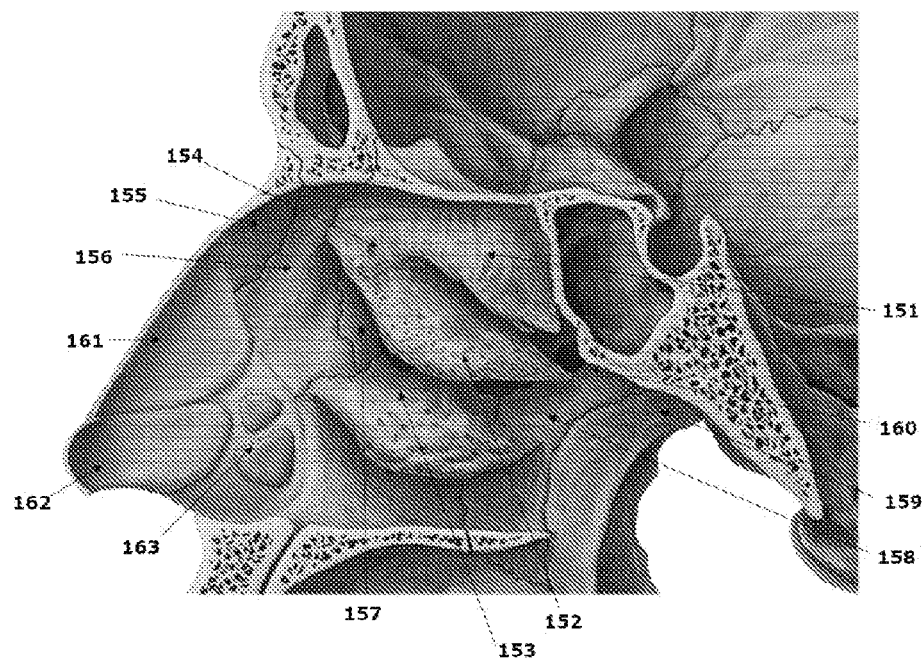
FIG. 1A illustrates the bone and cartilage anatomy of the lateral nose and nasal cavity.
Figure 1B:
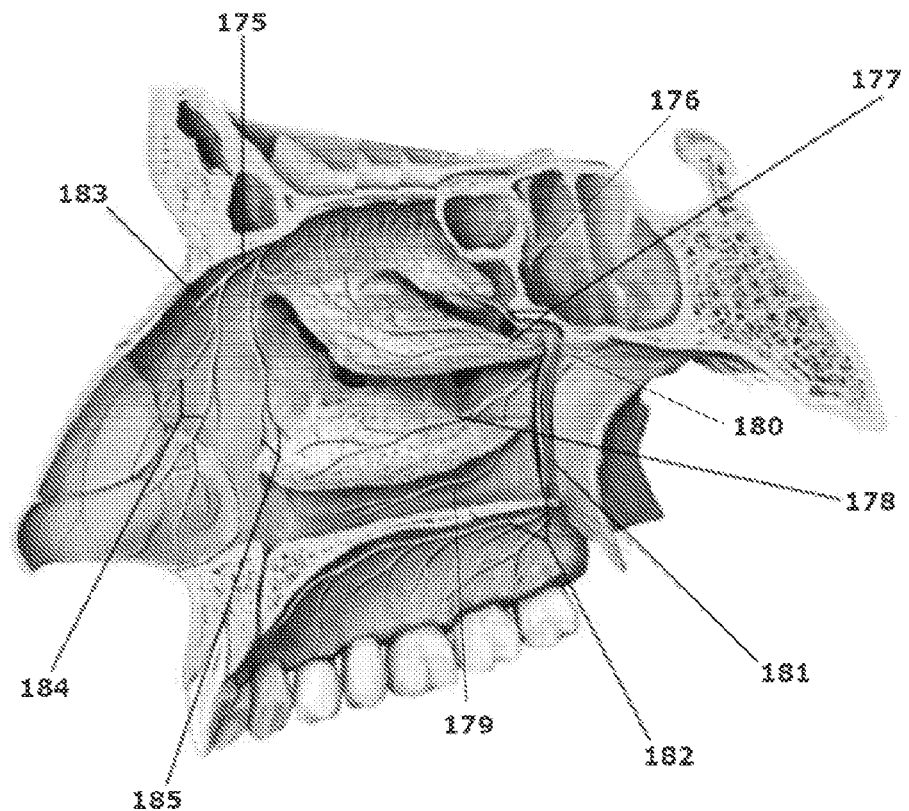
FIG. 1B illustrates the lateral wall of the nasal cavity and selected nerves and nerve branches.
Figure 1C:
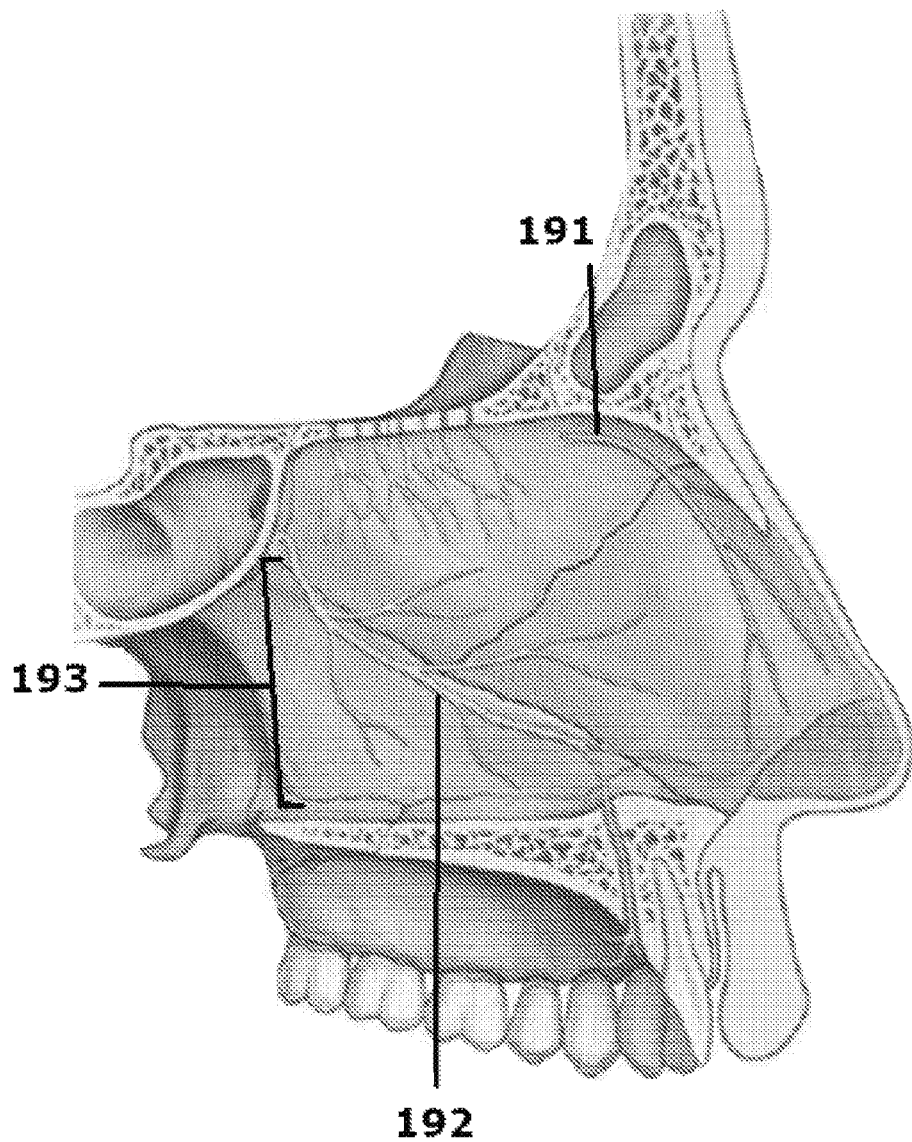
FIG. 1C illustrates the septal wall of the nasal cavity and selected nerves and nerve branches.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Disorders involving the nerves described above, as well as other nasal cavity nerves, have been linked to several clinical presentations. For example, many rhinitis symptoms, including runny nose, nasal congestion, sneezing, and itching, have been linked to abnormal neurological function. Conditions such as chronic pain, cluster headaches, and migraines are also known to be related to the nerves of the nasal cavity. As such, various treatments that alter these neural pathways have been shown to provide some degree of relief to patients that suffer from the above ailments. These treatments involve physically damaging the nerves (for example, by resection or removal), thermal ablation treatments, chemical alteration treatments, and other treatments. An example of therapies targeting nasal nerves to address these ailments are described in U.S. patent application Ser. No. 15/242,362 filed Aug. 19, 2016, entitled "APPARATUS AND METHODS FOR TREATING RHINITIS", which is incorporated herein by reference in its entirety for all purposes. Other examples are detailed in the following literature which are incorporated by reference: (i) Fang et al, "Nasal Endoscopy Combined With Multiple Radiofrequency for Perennial Allergic Rhinitis", Di Yi Jun Yi Da Xue Xue Bao. 2005 July; 25(7):876-7, Chinese, PubMed PMID: 16027090 (available at https://www.ncbl.nlm.nih.gov/pubmed/16027090); (ii) Feng et al., "The Clinical and Pathological Changes Following Anterior Ethmoid Neurotomy in Treating Perennial Allergic Rhinitis with Plasma", Lin Chuang Er Bi Yan Hou Ke Za Zhi. 2003 February; 17(2):97-9, Chinese. PubMed PMID: 12833694 (available at https://www.ncbi.nlm.nih.gov/pubmed/12833694); and (iii) Paulose, "Allergic Rhinitis-Nasal Allergy-Laser Treatment", available at https://drpaulose.com/general/allergic-rhinitis-nasal-allergy-laser-treatment.

A challenge in treating the disorders referenced above with nervous system-targeted therapies is accurately and sufficiently targeting all of the dysfunctional nerves and nerve branches. More specifically, in some cases, small and medium-sized branches of nerves have meaningful contributions to symptoms, and their coverage throughout the nasal mucosa is vast. A further challenge is that some disorders (e.g. rhinitis) could be caused by multiple dysfunctional nerves. For example, rhinitis includes four primary symptoms: runny nose (e.g., excessive mucus secretion, which may occur in anterior and/or posterior regions of the nasal cavity), nasal congestion (e.g., due to mucosa inflammation), itching (e.g., due to mucosa irritation), and sneezing. Mucus secretion and inflammation are controlled by the parasympathetic nerve fibers which emerge from the sphenopalatine ganglion, and itching and sneezing are controlled by the sensory nerve fibers of the anterior ethmoid nerve.

Some existing therapies for rhinitis target the parasympathetic nerve fibers in the posterior portion of the nose. This approach may address the runny nose and nasal congestion symptoms without addressing the innervation of the anterior or medial portions of the nose, leaving rhinitis sufferers with remaining symptoms either due to the AEN's sensory role that impacts itching and sneezing or its parasympathetic role that impacts mucus secretion. There are some documented attempts of targeting the AEN on the anterior portion of the nose for the treatment of rhinitis, but therapies have not been adopted due to either incomplete relief and/or relapse of symptoms.

There exists a need for systems and methods that provide more comprehensive treatment options for rhinitis and related ailments. These systems and methods may provide a more complete approach to targeting the nerves within the nasal cavity using thermal treatments or alternative interventions. More specifically, these systems and methods would be configured to target the AEN in addition to a combination of other sensory and parasympathetic nerves within the nasal cavity to provide more complete relief of rhinitis symptoms and other ailments due to nasal nerve disorders. Novel methods and enabling-devices along these lines would benefit patients and the healthcare system more broadly by providing better and longer-lasting relief of symptoms.

The present disclosure is related to systems, devices, and methods that can address one or more of the challenges associated with existing approaches and thereby improve treating ailments related to nasal nerve dysfunction, including rhinitis. More specifically, the present disclosure relates to systems and methods for targeting one or more nerve locations to be treated within the nasal cavity. In examples, the treatments involve thermal treatments such as, for instance, radiofrequency ablation and cryoablation. The disclosure can be particularly useful during cryotherapy procedures applied within the upper airway.

Various aspects of the disclosure described herein may be applied to any of the particular applications set forth below or for any other types of thermal or non-thermal treatment systems or methods. The disclosure may be applied as a standalone system or method, or as part of an integrated medical treatment system.

Figure 2:
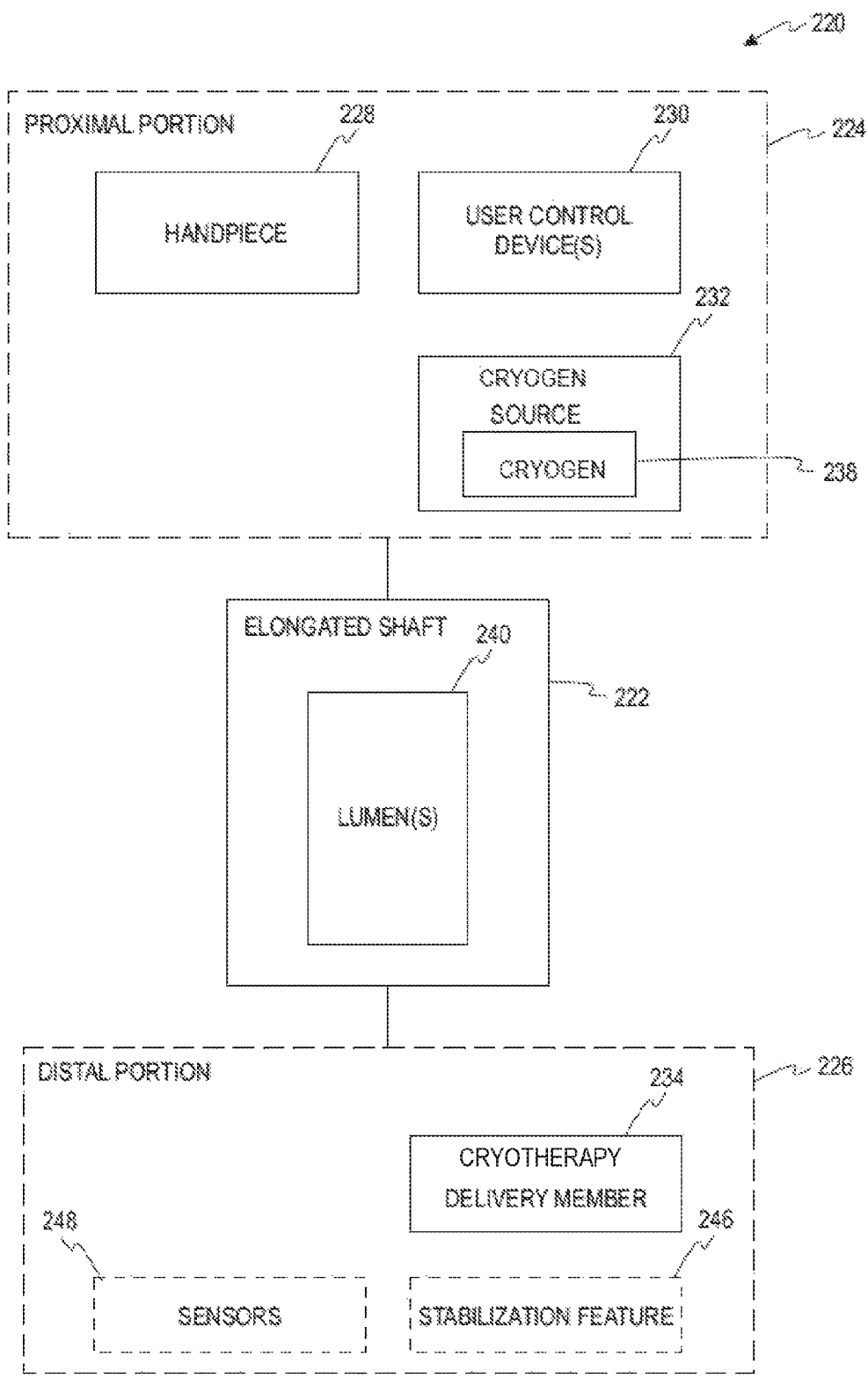
FIG. 2 shows a simplified block diagram of a cryotherapy device, according to an example.

Referring now to FIG. 2, a simplified block diagram of a cryotherapy device 220 is shown according to an example. As shown in FIG. 2, the cryotherapy device 220 includes an elongated shaft 222 that extends between a proximal portion 224 of the cryotherapy device 220 and a distal portion 226 of the cryotherapy device 220. The elongated shaft 222 can be configured to be at least partially inserted in a nasal cavity of a patient. For example, the elongated shaft 222 can have a diameter between approximately 1 millimeters (mm) and approximately 4 mm. Additionally, for example, the elongated shaft 222 can be made from at least one material chosen from stainless steel and a semi-rigid polymer (e.g., such as Nylon or Pebax).

Although the elongated shaft 222 is shown as being separate from the proximal portion 224 and the distal portion 226 in FIG. 2, the proximal portion 224 and/or the distal portion 226 of the cryotherapy device 220 can include respective portions of the elongated shaft 222. More generally, the proximal portion 224 can include one or more components of the cryotherapy device 220 that are located relatively farther away from a target tissue to be treated with cryotherapy, and the distal portion 226 can include one or more components of the cryotherapy device 220 that are located relatively closer to the target tissue to be treated with cryotherapy. As used herein, the term "target tissue" means a tissue that is to be treated with a thermal therapy (e.g. cryotherapy) during a medical procedure.

The proximal portion 224 can include a handpiece 228, one or more user control devices 230 (e.g., at least one device chosen from one or more triggers, one or more knobs, one or more triggers, one or more buttons, one or more switches, one or more levers, and one or more dials), and/or a cryogen source 232. The distal portion 226 can include a cryotherapy delivery member 234.

Within examples, the handpiece 228 can be configured to facilitate gripping and manipulating the cryotherapy device 220. For instance, the handpiece 228 can have a shape and/or a size that can facilitate a user manipulating the elongated shaft 222 and the distal portion 226 using a single hand. In one example, the handpiece 228 can have a shape and/or a size that facilitates the user holding the handpiece 228 in a pistol gripping manner (e.g., the handpiece 228 can have an axis that is transverse to an axis of the elongated shaft 222). In another example, the handpiece 228 can additionally or alternatively have a shape and/or a size that facilitates the user holding the handpiece 228 in a writing utensil gripping manner (e.g., the handpiece 228 can have an axis that is substantially parallel to an axis of the elongated shaft 222). Additionally or alternatively, the handpiece 228 can (i) facilitate gripping and manipulating the cryotherapy device 220 by having a shape and/or a size that is greater than a shape and/or a size of the elongated shaft 222 and/or (ii) allow the user to operate the user control device(s) 230 while gripping and manipulating the cryotherapy device 220 with a single hand.

The cryogen source 232 can store a cryogen 238. As examples, the cryogen 238 can include nitrous oxide, liquid nitrogen, or other cryogens used during medical procedures.

As shown in FIG. 2, the elongated shaft 222 can include one or more lumens 240 that couple the cryogen source 232 at the proximal portion 224 to the cryotherapy delivery member 234 at the distal portion 226. In general, the cryotherapy delivery member 234 is configured to use the cryogen 238 to apply thermal energy to the target tissue. In one example, the cryotherapy delivery member 234 can include a balloon into which the cryogen 238 (e.g., in the form of a compressed liquid) can expand as a gas. As another example, the cryotherapy delivery member 234 can include one or more metallic plates, which can be chilled through contact with the cryogen 238 (e.g., in the form of a circulating cooled fluid). In these examples, the cryotherapy delivery member 234 includes an intermediary member (e.g., the balloon and/or the metallic plate(s)) that transfers the thermal energy from the cryogen 238 to the target tissue. This can beneficially help to improve the uniformity of the distribution of cold temperatures applied across a targeted region of tissue. This indirect application of cooling can also prevent cryogen substances (e.g. saline, or other liquids or gases) from direct exposure to the body in unwanted regions. For example, cold saline applied directly to the nasal cavity would run down a patient's throat, causing discomfort and possible tissue injury in unwanted regions. However, in other examples, the cryotherapy delivery member 234 can apply the cryogen 238 directly to the target tissue.

In some implementations, the cryotherapy delivery member 234 can have an active surface that is configured for contacting the target tissue such that relatively little or no thermal energy is applied to tissue regions remote from the active surface. For example, the cryotherapy delivery member 234 can include the active surface and an inactive surface such that the cryotherapy delivery member 234 applies the thermal energy to the target tissue contacting the active surface and does not apply the thermal energy to other tissue contacting the inactive surface. This can help to apply thermal energy in a relatively targeted manner to treat a specific target tissue.

In other implementations, an entirety of the cryotherapy delivery member 234 can be active such that the cryotherapy delivery member 234 applies the thermal energy omnidirectionally. This can help to apply the thermal energy more broadly and, in some instances, can help to reduce a time for performing a cryotherapy procedure.

Within examples, the user control device(s) 230 can control a flow of the cryogen 238 from the cryogen source 232 to the cryotherapy delivery member 234. For instance, the user control device(s) 230 can include at least one device chosen from one or more knobs, one or more triggers, one or more buttons, one or more switches, one or more levers, and one or more dials that can be actuated to start, stop, increase, and/or decrease a flow of the cryogen 238 from the cryogen source 232 to the cryotherapy delivery member 234. Also, within examples, the user control device(s) 230 can be located on the handpiece 228 and/or at a location that is separate from the handpiece 228.

In some examples, the cryogen source 232 can be separate from the handpiece 228. For instance, the cryogen source 232 can include an external canister that contains the cryogen 238. The canister can be coupled to an infusion port on the handpiece 228 and a valve or alternate control device can be actuated to supply the cryogen 238 from the cryogen source 232 to the cryotherapy delivery member 234 (e.g., via the lumen(s) 240) and from the cryotherapy delivery member 234 to the target tissue. Thus, in this implementation, the pressure gradient established by opening the valve coupled to the cryogen source 232 can provide a pressure for delivering the cryogen 238 through the lumen(s) 240 and out the cryotherapy delivery member 234 to the target tissue.

In other examples, the cryogen source 232 can be integrated with the handpiece 228 and/or actuated by the user control device(s) 230. For instance, in one implementation, the cryogen source 232 can be a disposable reservoir or a reusable reservoir of a chilled circulating fluid that is housed in the handpiece 228. The cryogen source 232 can also include at least one device chosen from one or more valves and one or more pumps that facilitate supplying the cryogen 238 from the cryogen source 232 to the cryotherapy delivery member 234. The valve(s) and/or the pump(s) can be operable by the user control device(s) 230 to start, stop, increase, and/or decrease a flow of the cryogen 238 from the cryogen source 232 to the cryotherapy delivery member 234.

In some implementations, locating the cryogen source 232 in the handpiece 228 can beneficially provide for a relatively compact size of the cryotherapy device 220 by, for example, reducing or eliminating relatively long external connections (e.g., tubes and/or cables) between the handpiece 228 and the cryogen source 232. Whereas, in some implementations, locating the cryogen source 232 in a housing that is separate from the handpiece 228 can, among other things, beneficially allow the cryogen source 232 to store a relatively larger amount of the cryogen 238 without impairing the handling capabilities of the handpiece 228.

As shown in FIG. 2, the cryotherapy device 220 can also include one or more stabilizer features 246 and/or one or more sensors 248. For instance, in some examples, the cryotherapy device 220 can include the stabilizer features 246 to assist in retaining the cryotherapy device 220 at a relatively fixed position while providing cryotherapy to a target tissue. As described in further detail below, the stabilizer features 246 can include a suction device that can apply suction to a tissue in the nasal cavity and/or an expandable member (e.g., a balloon) that can expand engage tissue adjacent to the target tissue.

The sensor(s) 248 can facilitate positioning the cryotherapy device 220 such that the distal portion 226 contacts a particular type of tissue and/or anatomical structure in the nasal cavity (e.g., a nasal cavity wall). For instance, the sensor(s) 248 can be located on the distal portion 226 of the cryotherapy device 220. As examples, the sensor(s) 248 can include at least one sensor chosen from one or more pressure sensors or load cells, one or more temperature-sensitive elements, one or more impedance monitoring elements, and one or more distance measurement sensors such as one or more ultrasound-based distance sensors or one or more IR-based distance sensors.

The cryotherapy device 220 can be used to perform a medical procedure on the target tissue in the nasal cavity. For example, in operation, the cryotherapy device 220 can be inserted in the nasal cavity to position the distal portion 226 adjacent to the AEN 175 (e.g., over a nasal bone and/or on a septum) or the posterior nasal nerves 176-180. After the distal portion 226 is positioned in proximity to the target tissue, the user control device(s) 230 can be operated to cause the cryotherapy delivery member 234 to deliver cryotherapy to a target tissue. For instance, the user control device(s) 230 can cause a valve to open such that a cryogen moves along a lumen 240 from a proximal portion 224 of the cryotherapy device 220 to the distal portion 226 of the cryotherapy device 220 containing the cryotherapy delivery member 234. The cryotherapy delivery member 234 can use the cryogen 238 to apply the thermal energy to the target tissue to alter the target tissue and treat one or more conditions.

FIGS. 3A-6C show a plurality of implementations that can be instituted in connection with the cryotherapy device 220 shown in FIG. 2, according to examples of the present disclosure. In particular, FIGS. 3A-6C show various example implementations for the elongated shaft 222, the distal portion 226, and/or the cryotherapy delivery member 234 shown in FIG. 2.

Figure 3A:
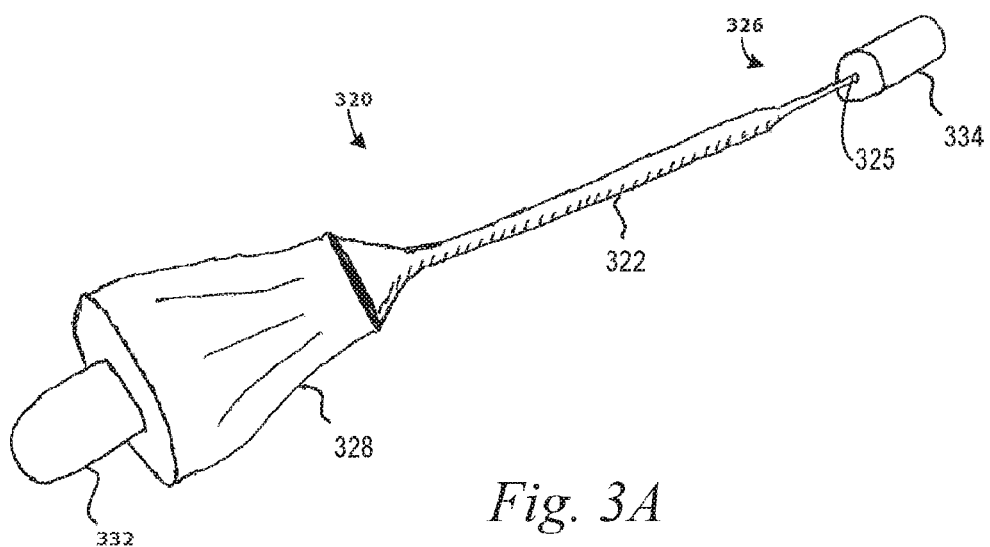
FIG. 3A illustrates a cryotherapy device, according to an example.

Referring now to FIG. 3A, a cryotherapy device 320 is shown according to an example. The cryotherapy device 320 is substantially similar or identical to the cryotherapy device 220 shown in FIG. 2. As shown in FIG. 3A, the cryotherapy device 320 includes a cryotherapy delivery member 334 coupled to a distal end 325 of an elongated shaft 322. The proximal portion of the cryotherapy device 320 includes a handpiece 328 and a cryogen source 332, which is configured to house a cryogen (e.g., the cryogen 238). As described above, the elongated shaft 322 can include the one or more lumens (e.g., the lumen(s) 240) that fluidly couple the cryotherapy delivery member 334 to the cryogen source 332.

In examples, the elongated shaft 322 of the cryotherapy device 320 is malleable and/or flexible. This can beneficially allow a shape of the elongated shaft 322 to be customized according to a patient's specific anatomy, and for the configuration of the device 320 to be altered based upon the target treatment site(s) for a specific patient. As examples, the elongated shaft 322 may be composed of at least one material chosen from aluminum, annealed stainless steel, and copper. The distal portion 326 terminates with a cryotherapy delivery member 334. In examples, the cryotherapy delivery member 334 may consist of an inflatable balloon or an otherwise expandable region capable of transitioning between an initial collapsed state with a first diameter to an expanded state with a second diameter, where the first diameter is smaller than the second diameter. The capability for the distal portion 326 to have an expandable configuration can beneficially allow for improved maneuverability through small spaces such as the nasal cavity during placement proximate to a target treatment site (e.g., proximate to the AEN) while in the smaller collapsed state, while also preserving the ability to treat a larger area of tissue if cryotherapy is delivered with the cryotherapy delivery member 334 expanded into the larger expanded state. An additional advantage of a balloon and/or otherwise expandable cryotherapy delivery member 334 is the possibility to omnidirectionally deliver cryotherapy to tissues on both the lateral and medial sides of the distal portion 326 of the cryotherapy device 320. In example implementations that utilize a cryotherapy delivery member 334 configured as a balloon, the balloon may be of the compliant type and comprised of one or more materials such as, for instance, silicone, latex, nylon, or other similar materials.

The handpiece 328 contains a cryogen source 332 such as, for example, a cryogen source configured to interface with a canister containing a liquid cryogen. In examples, a liquid cryogen enters the elongated shaft 322 through a lumen (e.g., the lumen(s) 240) via the cryogen source 332 when the user opens a valve using a control device (not shown, e.g. similar to user control device(s) 230 described above) on handpiece 328, said cryogen expanding into a gas as it exits the elongated shaft 322 via fenestrations (not shown) near the distal end 325. This expansion into a gas may cause the cryotherapy delivery member 334 to expand and also create a source of cold energy which can be transferred to tissues via contact with the cryotherapy delivery member 334.

In alternate implementations, the cryotherapy delivery member 334 may be expanded with air, a gas, a fluid, or by other means prior to releasing the cryogen into the distal portion 326 of the cryotherapy device 320. In further alternative implementations, other cryogenic methods—for example circulation of a cold fluid, or using thermoelectric devices that employ the Peltier effect—may be utilized by the cryotherapy device 320, and the device configuration may be adapted for use with these alternative methods.

Figure 3B:
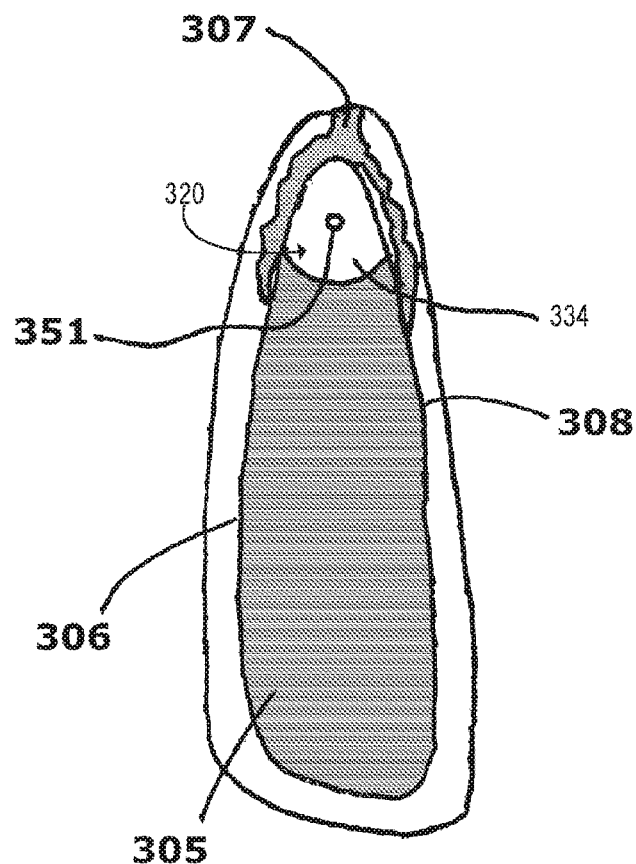
FIG. 3B illustrates the device of FIG. 3A positioned in the nasal cavity of a patient, according to an example.

FIG. 3B is a cross-sectional view of the cryotherapy device 320 shown in FIG. 3A placed within a portion of the nasal cavity 305, which is shown in a coronal cross-section. The thickness and relative size of certain regions of the nasal anatomy are not drawn to scale in FIG. 3B. The lateral nasal cavity wall 306 and the septal nasal cavity wall 308 of the nasal cavity 305 are shown. Also shown is a nerve 307 (e.g., the AEN 175) that exists in the mucosal/sub-mucosal tissue regions proximate to the superior portion of the nasal cavity 305. Nerve 307 descends into both the lateral and septal regions of the nasal cavity 305. In at least some humans, the anterior ethmoid nerve or branches/portions of the anterior ethmoid nerve may have a structure that is similar to that shown for nerve 307.

FIG. 3B shows the distal portion 326 of the cryotherapy device 320 indicated in FIG. 3A. The cryotherapy delivery member 334 is shown in an expanded state projecting radially from a central axis 351 which is part of the distal portion 326. In the expanded state, the cryotherapy delivery member 334 can establish contact with a plurality of tissue surfaces. In the present example, the cryotherapy delivery member 334 simultaneously establishes contact with both the lateral nasal cavity wall 306 and the septal nasal cavity wall 308, as well as with the superior aspect of the nasal cavity 305. Accordingly, use of the cryotherapy device 320 in the manner shown enables simultaneous treatment of multiple branches of nerve 307. This is valuable because it provides for a more thorough treatment of relevant nasal anatomy compared to a device that can only treat one branch of a nerve, and because it shortens the total treatment time due to the one-shot nature of the therapy delivered to multiple nerve branches.

FIGS. 4A-4D show a distal portion of a cryotherapy device 420 according to another example. The cryotherapy device 420 includes a cryotherapy delivery member 434 that is actuatable between (i) a first configuration in which the cryotherapy delivery member 434 has a collapsed state and (ii) a second configuration in which the cryotherapy delivery member 434 has an expanded state. In the collapsed state, the cryotherapy delivery member 434 can have a relatively small profile (e.g., a relatively slim profile) and, in the expanded state, the cryotherapy delivery member 434 can have a relatively larger profile (e.g., an expanded profile). In this arrangement, the cryotherapy delivery member 434 can be in the first configuration to facilitate inserting the cryotherapy device 420 to a target tissue, and the cryotherapy delivery member 434 can be in the second configuration at the target tissue to apply cryotherapy to the target tissue.

Figure 4A:
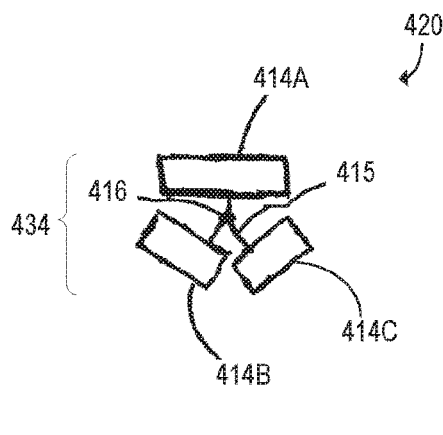
FIG. 4A illustrates the distal end of a cryotherapy device with the delivery tip in a first, collapsed position, according to an example.
Figure 4B:
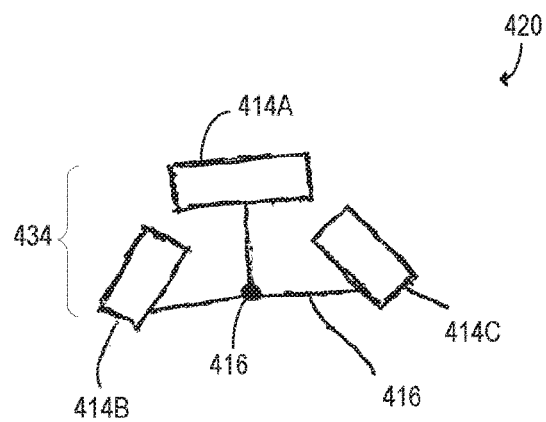
FIG. 4B illustrates the distal end of the cryotherapy device of FIG. 4A with the delivery tip in a second, expanded position, according to an example.

In FIGS. 4A-4D, the cryotherapy delivery member 434 includes a plurality of plates 414A-414C that are moveable relative to each other. For example, as shown in FIGS. 4A-4B, the cryotherapy delivery member 434 can include a plurality of rods 415 that couple the plates 414A-414C to an adjustable pivot point 416. The rods 415 and/or the adjustable pivot point 416 can be configured to adjust at least one condition chosen from a position, a distance, and an angle of the plates 414A-414C relative to each other (and/or relative to the adjustable pivot point 416). In some examples, the adjustable pivot point 416 and/or the rods 415 can be configured such that each plate 414A-414C is independently moveable relative to the other plates 414A-414C. In other examples, the adjustable pivot point 416 and/or the rods 415 can be configured such that at least two of the plates 414A-414C move together. For instance, in such examples, moving one plate 414A-414C can cause a corresponding movement of at least one other plate 414A-414C.

FIG. 4A illustrates an end-on view of the distal portion of the cryotherapy device 420 in the first configuration in which a cryotherapy delivery member 434 of the cryotherapy device 420 has the relatively slim profile in the collapsed state. In response to the user manipulating a control feature on the handpiece (e.g., the user control device(s) 230 on the handpiece 228 shown in FIG. 2) of the cryotherapy device 420, the cryotherapy delivery member 434 can be adjusted to the second, expanded configuration, which is illustrated in FIG. 4B. As shown in FIGS. 4A-4B, the positions, the distances, and/or the angles of the rods 415 (relative to the adjustable pivot point 416) have been altered to adjust the respective positions of the plates 414A-414C (relative to the adjustable pivot point 416).

Figure 4C:
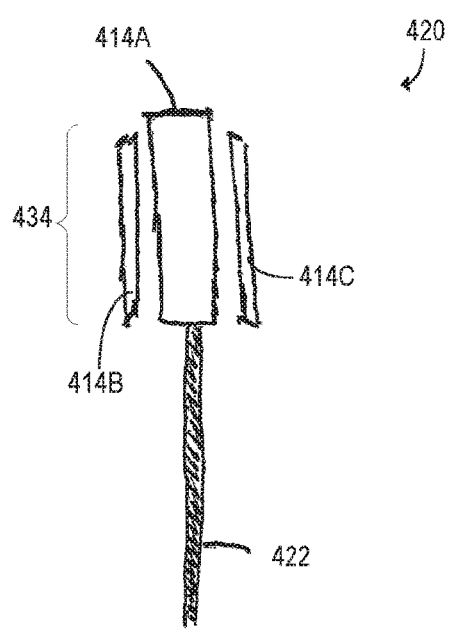
FIG. 4C illustrates a different view of the cryotherapy device of FIG. 4A, according to an example.
Figure 4D:
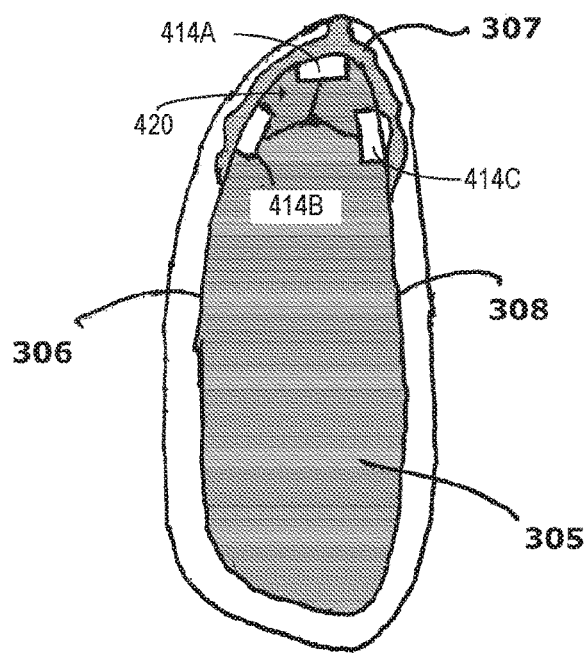
FIG. 4D illustrates the device of FIG. 4A positioned in the nasal cavity of a patient, according to an example.

Additionally, as shown in FIGS. 4A-4B and 4D, an angular orientation of plates 414A-414C may change as the connecting rods 415 move the plates 414A-414C such that an active side of the plates 414A-414C faces outward in a direction of the target tissue to be treated. That is, an angle between each plate 414A-414C and the respective rod 415 coupled to the plate 414A-414C can be adjusted at a joint coupling the plate 414A-414C to the respective rod 415. For instance, the joint can be a multi-axis joint that facilitates adjusting the angular orientation of the plates 414A-414C relative to the rods 415. In some examples, the angular orientation of the plates 414A-414C can be adjusted passively (e.g., by weighting the plates 414A-414C such that gravitational forces rotate the plates 414A-414C to specific angles with each position of the rods 415). In examples, the active side of each plate 414A-414C can pivot at the joint in order adjust to accommodate the position of the wall. In examples, the plates 414A-414C and the rods 415 may be covered or encased in a thermally-conductive external structure, for example within the lumen of a thin-walled catheter.

FIG. 4C depicts a top view of the distal end of the cryotherapy device 420 shown in FIGS. 4A-4B. As shown in FIG. 4C, the cryotherapy device 430 can include an elongated shaft 422 which connects the distal portion of the cryotherapy device 420 to a proximal portion of the cryotherapy device 420 (e.g., the proximal portion 224 shown in FIG. 2). As also shown in FIG. 4C, the plates 414A-C may be elongated in a plane of the elongated shaft 422. For instance, as shown in FIG. 4C, the plates 414A-414C can have a length that is parallel to a longitudinal axis of the elongated shaft 422 and longer than a cross-sectional thickness of the plates 414A-414C in a plane transverse to the longitudinal axis.

In FIG. 4C, the cryotherapy device 420 is shown with the cryotherapy delivery member 434 in the second configuration (in which the cryotherapy delivery member 434 has the expanded state) with the plates 414A-414C angled outward towards the target tissue. A cryogen source (e.g., the cryogen source 232 in FIG. 2) may supply cryogen towards the plates 414A-414C in the distal end via one or more lumens (e.g., the lumen(s) 240 in FIG. 2) internal to elongated shaft 422. The cryogen source may be in direct contact with the plates 414A-C or may be delivered proximate to the plates 414A-414C with cold temperatures reaching the plates 414A-414C via thermal conduction, convection, or other means (e.g., the cryogen may be delivered to reservoirs separate from and adjacent to the plates 414A-414C such that the cryogen does not directly contact the plates 414A-414C).

FIG. 4D shows a cross-sectional view of the cryotherapy device 420 depicted in FIGS. 4A-4C positioned in a location in the nasal cavity. The cryotherapy device 420 is shown with the cryotherapy delivery member 434 in the second configuration (in which the cryotherapy delivery member 434 has the expanded state) with the plates 414A-414C in contact with nasal tissue in addition to the primary plate 414. The cryotherapy device 420 contacts both the lateral nasal cavity wall 306 and the septal nasal cavity wall 308 of the nasal cavity 305, as well as contacts the superior aspect of the nasal cavity. The plates 414A-414C may establish contact with tissue at several anatomical locations proximate to the nerve 307 (e.g., the AEN), which is shown to have branches that reach both the lateral nasal cavity wall 306 and the septal nasal cavity wall 308 of the nasal cavity 305.

In examples, a user can inactivate one or more of the plates 414A-414C using a user control device (e.g., the user control device(s) 230) on a handpiece of the cryotherapy device 420, allowing for selective treatment of a tissue region while sparing other regions. As such, the plates 414A-414C can be actuatable independently of each other to selectively apply thermal energy of cryotherapy using a subset of the plurality of plates 414A-414C.

For instance, in one example, the plate 414A can be a primary active face of the cryotherapy delivery member 434, with the plates 414B-414C acting as secondary active faces. In one implementation, the plate 414A can be deployed and/or activated first to apply cryotherapy using only the plate 414A. After applying the cryotherapy using only the plate 414A, at least one plate chosen from the plate 414B and the plate 414C can be deployed and/or activated to selectively apply cryotherapy to different locations in the nasal cavity. This can facilitate selectively applying cryotherapy to at least one target chosen from a plurality of different nerves and a plurality of different branches of a nerve without removing the cryotherapy device 420 from the nasal cavity during a given surgical procedure.

In some examples, both plates 414B, 414C may change in at least one condition chosen from position, distance, and angle when the cryotherapy delivery member 434 is actuated between the first configuration and the second configuration. In examples, the plate 414A may alternatively or additionally change in at least one condition chosen from position, distance, and angle, either in absolute terms or relative to at least one of the plates 414B-414C.

Although the plate 414A is the primary active face and the plate 414B and the plate 414C are the secondary active faces in the example described above, the plate 414A can be a secondary active face or the plate 414B and/or the plate 414C can be a primary active face in other examples. More generally, at least one of the plates 414A-414C can be the primary active face(s) and at least one of a remainder of the plates 414A-414C can be the secondary active face(s) in examples in which the cryotherapy device 420 is configured to have primary active faces and secondary active faces.

In examples, some plates 414A-414C may be adapted to deliver warming energy while others are adapted to deliver cooling energy, which allows for some tissue regions to be actively protected from incidental unwanted cooling energy.

In FIGS. 4A-4D, the cryotherapy delivery member 434 includes three plates 414A-414C. However, in other examples, the cryotherapy delivery member 434 can include a different quantity of plates 414A-414C.

FIG. 5 shows the distal portion of a cryotherapy device 520 according to another example. More specifically, FIG. 5 shows a sagittal plane view of the cryotherapy device 520 in a nasal cavity proximate to a lateral nasal cavity wall 506. Two tissue regions containing one or more nerves or nerve branches are shown, a posterior region 501 which may contain nerves such as the posterior nasal nerves (PPNs) or accessory posterior nasal nerves (APNNs), and an antero-superior region 502 which may contain nerves such as the AEN.

The cryotherapy device 520 includes an elongated shaft 522 that connects the distal portion of the cryotherapy device 520 to a proximal portion (e.g., the proximal portion 224 in FIG. 2) of the cryotherapy device 520. Within examples, the elongated shaft 522 can be flexible. As noted above, the proximal portion 224 of the cryotherapy device 520 may include the handpiece, the user control device(s), the cryogen source 232, the sensors 248 (e.g., camera monitors), and/or other features and components.

As shown in FIG. 5, the distal portion of the cryotherapy device 520 is bifurcated to facilitate treating at least one target chosen from a plurality of nerves and a plurality of different branches of a nerve in the nasal cavity. For instance, in FIG. 5, the elongated shaft 522 can be bifurcated into a first section 522A that is coupled to a first cryotherapy delivery member 534A, and a second section 522B that is coupled to a second cryotherapy delivery member 534B. Accordingly, in this example, the cryotherapy delivery member 234 shown in FIG. 2 is implemented as a plurality of cryotherapy delivery members 534A-534B, including the first cryotherapy delivery member 534A and the second cryotherapy delivery member 534B.

In FIG. 5, the first section 522A of the elongated shaft 522 can position the first cryotherapy delivery member 534A at the posterior region 501 of the nasal cavity to target a first nerve or a first branch of a nerve, and the second section 522B of the elongated shaft 522 can position the second cryotherapy delivery member 534B at the antero-superior region 502 of the nasal cavity to target a second nerve or a second branch of the nerve. In an example, the first cryotherapy delivery member 534A and the second cryotherapy delivery member 534B can be independently moveable relative to each other. For instance, the first section 522A and the second section 522B of the elongated shaft 522 can be independently steered using a user control device (e.g., the user control device(s) 230) on or near the handpiece. In another example, only one section 522A-522B, (e.g., the second section 522B, which is anterior of the first section 522A) is steerable directly, while the other section 522A-522B (e.g. the first section 522A) is inserted and navigated into place while maintaining a substantially unbent configuration.

Within examples, at least one section chosen from the first section 522A and the second section 522B of the elongated shaft 522 can be moveable to arrange the distal portion of the cryotherapy device 520 in a collapsed state. For instance, in the collapsed state, (i) the first section 522A and the first cryotherapy delivery member 534A and (ii) the second section 522B and the second cryotherapy delivery member 534B can be substantially co-aligned so as to present a slim profile cross-section to facilitate insertion of the cryotherapy device 520 into the nasal cavity and/or removal of the cryotherapy device 520 from the nasal cavity.

Additionally, within examples, a user can inactivate one or more of the first cryotherapy delivery member 534A and the second cryotherapy delivery member 534B using a user control device (e.g., the user control device(s) 230) on a handpiece of the cryotherapy device 520, allowing for selective treatment of a tissue region while sparing other regions. As such, the first cryotherapy delivery member 534A and the second cryotherapy delivery member 534B can be actuatable independently of each other to selectively apply thermal energy of cryotherapy using only one of the first cryotherapy delivery member 534A and the second cryotherapy delivery member 534B. Additionally or alternatively, the first cryotherapy delivery member 534A and the second cryotherapy delivery member 534B can be actuatable at the same time to simultaneously apply thermal energy of cryotherapy using both of the first cryotherapy delivery member 534A and the second cryotherapy delivery member 534B.

In a method of use, the cryotherapy device 520 is inserted into the nasal cavity and the first section 522A of the elongated shaft 522 is navigated to the posterior region 501 of the nasal cavity such that the first cryotherapy delivery member 534A is positioned proximate to the first nerve and/or the first branch of a nerve (e.g., in the posterior region 501). After positioning the first cryotherapy delivery member 534A, the user manipulates a user control device to adjust a position of the second section 522B of the elongated shaft 522 such that the second cryotherapy delivery member 534B is positioned proximate to the second nerve and/or the second branch of the nerve (e.g., in the antero-superior region 502). In some implementations, positioning the first cryotherapy delivery member 534A and the second cryotherapy delivery member 534B can be aided by a visualization technique such as with a fiberscope. In some examples, the method can include using a stabilization feature such as vacuum suction to maintain the position of first cryotherapy delivery member 534A while positioning the second cryotherapy delivery member 534B. While the first cryotherapy delivery member 534A and the second cryotherapy delivery member 534B in the above-described positions, a cryogen source may be activated and cryotherapy can be applied to targeted tissue regions.

Figure 6C:
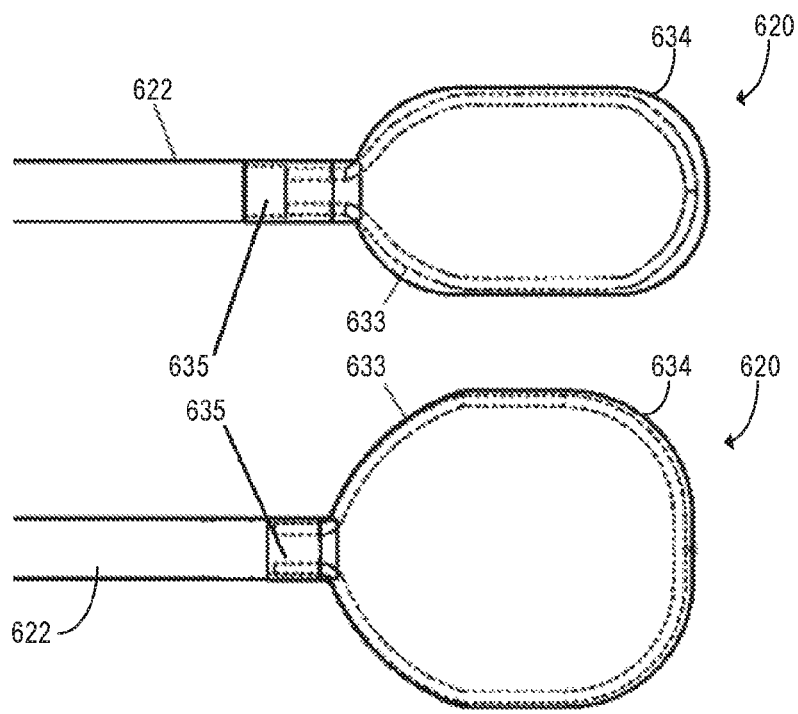
FIG. 6C illustrates a second view of the distal portion of the cryotherapy device shown in FIG. 6A in first and second configurations, according to an example.

Referring to FIGS. 6A-6D, a cryotherapy device 620 is shown according to another example. The cryotherapy device 620 is substantially similar or identical to the cryotherapy device 220 shown in FIG. 2. For instance, as shown in FIG. 6A, the cryotherapy device 620 includes a cryotherapy delivery member 634 coupled to a distal end of an elongated shaft 622. The proximal portion of the cryotherapy device 620 includes a handpiece 628. As described above, the elongated shaft 622 can include the one or more lumens (e.g., the lumen(s) 240) that fluidly couple the cryotherapy delivery member 634 to a cryogen source.

In FIGS. 6A-6D, the elongated shaft 622 is a multi-configurable cannula that includes a plurality of configurable segments, which can be manipulated using a user control device (e.g., the user control device(s) 230) on the handpiece 628. This can beneficially allow for the user to manipulate the position and/or shape of the cryotherapy device 620 without removing the distal end of the cryotherapy device 620 and/or the cryotherapy delivery member 634 from the nasal cavity, which saves time and improves patient comfort when it is desired to apply cryotherapy to multiple target tissue regions.

FIG. 6A shows the distal portion of the cryotherapy device 620. In this example, the elongated shaft 622 includes a proximal portion 622A having a fixed shape and a distal portion 622B that can be articulated relative to the proximal portion 622A of the elongated shaft 622. For instance, in FIG. 6A, the elongated shaft 622 includes an articulation joint 623 that couples the proximal portion 622A to the distal portion 622B of the elongated shaft 622. Within examples, the articulation joint 623 can be configured to articulate the distal portion 622B relative to the proximal portion 622A in a horizontal plane 627A and/or a vertical plane 627B relative to a longitudinal axis 629 of the proximal portion 622A of the elongated shaft 622 shown in FIG. 6B.

In an example, the distal portion 622B of the elongated shaft 622 can articulate along the horizontal plane 627A to either side of the longitudinal axis 629. For instance, in one implementation, the distal portion 622B of the elongated shaft 622 can articulate approximately 1 millimeters (mm) to approximately 20 mm in either direction along the horizontal plane 627A. Also, as an example, the proximal portion 622A of the elongated shaft 622 can be substantially straight between the proximal portion 624 and the articulation joint 623, which can be located approximately 15 mm to approximately 45 mm from a distal end of the cryotherapy device 620.

As an example, in FIG. 6A, the distal portion 622B of the elongated shaft 622 and the cryotherapy delivery member 634 are shown in a first position 631A depicted by solid lines, and a second position 631B depicted by phantom lines. As shown in FIG. 6A, when the cryotherapy delivery member 634 is in the first position 631A, the distal portion 622B of the elongated shaft 622 is substantially axially aligned with the proximal portion 622A of the elongated shaft 622. As also shown in FIG. 6A, when the cryotherapy delivery member 634 is in the second position 631B, the distal portion 622B is flexed at the articulation joint 623 such that the cryotherapy delivery member 634 is offset in the horizontal plane 627A relative to the first position 631A of the cryotherapy delivery member 634.

Within examples, the articulation joint 623 can additionally or alternatively provide for articulating the distal portion 622B of the elongated shaft 622 in the vertical plane 627B relative to the longitudinal axis 629 of the cryotherapy device 620. For instance, in one implementation, the distal portion 622B of the elongated shaft 622 can articulate approximately 1 millimeters (mm) to approximately 20 mm in either direction along the vertical plane 627B.

In examples, articulating the distal portion 622B relative to the proximal portion 622A of the elongated shaft 622 can be achieved using one or more pull wires (not shown) that are affixed to the elongated shaft 622 proximal to the cryotherapy delivery member 634 (e.g., at the proximal portion 622A of the cryotherapy device 620). For instance, the proximal portion 622A of the elongated shaft 622 can be flexed responsive to the user actuating the pull wire(s). As examples, the distal portion 622B can be constructed of at least one structure chosen from a multi-lumen polymer tube, a stainless steel stacked coil, and a laser cut hypotube to achieve a suitable flexibility and column strength to enable navigation of the elongated shaft 622 around structures in the nasal cavity.

Within examples, the cryotherapy device 620 can additionally or alternatively adjust a size of the cryotherapy delivery member 634. In examples, the cryotherapy delivery member 634 can adjust the size of the cryotherapy delivery member 634 independently of the position adjustments of the elongated shaft 622 described above.

In examples, the cryotherapy delivery member 634 can change size in the vertical plane 627B without a corresponding size change in the horizontal plane 627A. In examples, the cryotherapy delivery member 634 can expand in size by approximately 2 mm to approximately 20 mm in the vertical plane 627B without a corresponding expansion in the horizontal plane 627A. This unidirectional expansion capability can beneficially allow the user to adjust the cryotherapy treatment area while keeping the cryotherapy delivery member 634 relatively slim in width in the horizontal plane 627A, which facilities positional changes in tight spaces such as the nasal cavity.

Within examples, a user can change the size and/or a shape of the elongated shaft 622 and/or cryotherapy delivery member 634 at any time during a cryotherapy procedure. In an example method of use, the size of the cryotherapy delivery member 634 can be changed immediately prior to delivery of the thermal therapy and after the cryotherapy device 620 has been navigated into the approximate desired position for treatment. This method of use allows the user confirm treatment size and location prior to initiating cryotherapy.

With reference to FIG. 6C, the distal portion of the cryotherapy device 620 is shown in a collapsed state (top) and an expanded state (bottom). In the collapsed state, the cryotherapy delivery member 634 is in a relatively smaller, compact configuration. In the expanded state, the cryotherapy delivery member 634 is in a second configuration where it has expanded size in the vertical plane 627B. Accordingly, the cryotherapy delivery member 634 has a first size in the collapsed state, the cryotherapy delivery member 634 has a second size in the expanded state, and the first size is smaller than the second size.

In an example, the cryotherapy delivery member 634 includes a uniplanar member 633 that can be constructed from a semi-flexible material such as, for instance, at least one material chosen from a nylon plastic, nitinol alloy, and stainless steel such that the cryotherapy delivery member 634 is expandable only in a pre-defined plane (e.g., the vertical plane 627B). The example shown also includes a translatable element 635 that resides with a body of the elongated shaft 622 and is coupled to the uniplanar member 633. A position of the translatable element 635 along the elongated shaft 622 may be adjusted via a user by manipulating a user control device on the handpiece (not shown). In an example, the user may manipulate a dial, slider, switch, or other suitable feature on the handpiece which causes translatable element 635 to shift from a first position which is relatively closer to the proximal end of the cryotherapy device 620 to a second position which is relatively closer to the cryotherapy delivery member 634. As the translatable element 635 moves distally along the elongated shaft 622 closer to the cryotherapy delivery member 634, the translatable element 635 applies a force to the uniplanar member 633 which causes the uniplanar member 633 (and thus the cryotherapy delivery member 634) to expand in the vertical plane 627B of the cryotherapy device 620.

Figure 6D:
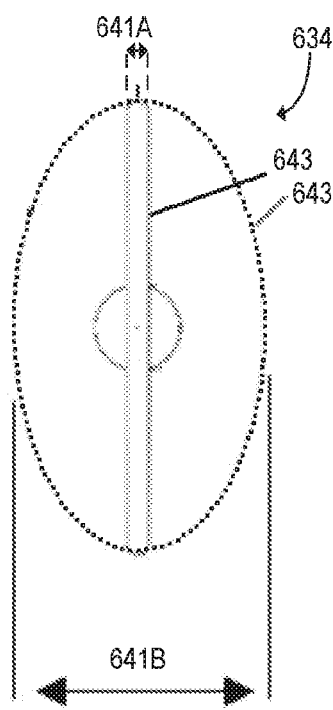
FIG. 6D illustrates a third view of the distal portion of the cryotherapy device shown in FIG. 6A in first and second configurations, according to an example.

In examples, the cryotherapy delivery member 634 may additionally or alternatively expand in the horizontal plane 627A with respect to the longitudinal axis 629 of the elongated shaft 622 of the cryotherapy device 620. As an example, FIG. 6D shows the cryotherapy delivery member 634 in two states: a collapsed state (indicated by solid lines) and an expanded state (indicated by phantom lines). As shown in FIG. 6D, when the cryotherapy delivery member 634 is in the expanded state, the cryotherapy delivery member 634 has a first width 641A in the horizontal plane 627A. In FIG. 6D, when the cryotherapy delivery member 634 is in the expanded state, the cryotherapy delivery member 634 has a second width 641B in the horizontal plane 627A. The second width 641B is greater than the first width 641A such that the cryotherapy delivery member 634 can have a relatively slim profile in the collapsed state and a relatively larger profile in the expanded state. Additionally, an exterior surface 643 of the cryotherapy delivery member 634 covers a larger width when the cryotherapy delivery member 634 is in the expanded state.

In an example method of use, the cryotherapy device 620 can be initially configured with the cryotherapy delivery member 634 in the collapsed state such that the cryotherapy delivery member 634 has the first width 641A. While the cryotherapy delivery member 634 is in the collapsed state, the elongated shaft 622 can be inserted into the nose and the cryotherapy delivery member 634 can be placed against the mucosa of the septum proximate to the bony section (just posterior to the cartilage portion of the anterior portion of the nose) opposite of the agger nasi cells of the lateral wall. The cryotherapy delivery member 634 is then horizontally expanded to the expanded state (such that the cryotherapy delivery member 634 has the second width 641B) using a user control device on or proximate to the handpiece until the exterior surface 643 of the cryotherapy delivery member 634 contacts the lateral nasal wall. The uniplanar member 633 can be adjusted by the user (using the user control device(s) on or proximate to the handpiece) to ensure the exterior surface 643 does not contact the arch of the nose. The thermal therapy is then delivered to treat both the internal nasal branch 185 and septal branch 191 of the AEN, for example for a duration between approximately 5 seconds and approximately 60 seconds. In another example, the duration can be between approximately 10 seconds and approximately 30 seconds.

After cryotherapy has been delivered, a user can return the cryotherapy delivery member 634 to the collapsed state by manipulating the user control device(s) on or proximate to the device handpiece. While the cryotherapy delivery member 634 is in the collapsed state, the cryotherapy device 620 can be advanced posteriorly further into the nasal cavity. As the distal end of the cryotherapy delivery member 634 approaches the middle meatus, a position of the distal portion 622B of the elongated shaft 622 can be adjusted such that the elongated shaft 622 bends at the articulation joint 623 to position the cryotherapy delivery member 634 to the lateral side of the middle turbinate while the majority of the elongated shaft 622 (e.g., the proximal portion 622A of the elongated shaft 622) remains in a center of the nasal cavity.

The cryotherapy delivery member 634 can then be advanced posteriorly until a distal end of the cryotherapy delivery member 634 contacts the most posterior attachment of the middle turbinate to the lateral wall. Once contact is made between the cryotherapy delivery member 634 and the most posterior attachment of the middle turbinate to the lateral wall, a position of uniplanar member 633 can be adjusted so as to adjust the size of cryotherapy delivery member 634 (e.g., in the vertical plane 627B) in order to ensure sufficient coverage of the palatine bone and the mucosa just inferior to the sphenopalatine foramen. After the size of the cryotherapy delivery member 634 is adjusted, the cryotherapy device 620 can apply cryotherapy to the PNNs and APNN on the lateral wall and lateral side of the middle turbinate. The duration of the cryotherapy therapy can be similar to that the durations described above for the anterior side of the nasal cavity. Optionally, the cryotherapy delivery member 634 can then be repositioned into the inferior meatus in a similar manner as described above for the middle meatus. For treatments targeting the inferior meatus, the size of the cryotherapy delivery member 634 can be collapsed and a degree of articulation of the distal portion 622B of the elongated shaft 622 (relative to the proximal portion 622A) may be reduced relative to treatments in the middle meatus.

Figure 7:
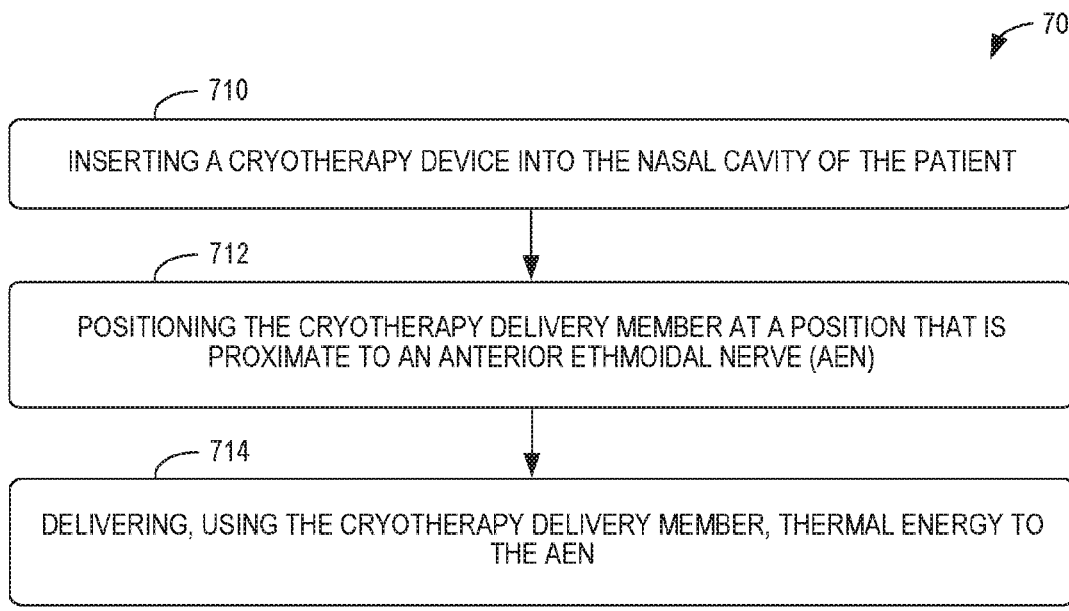
FIG. 7 illustrates a flowchart for a process for applying cryotherapy to a target tissue in a nasal cavity of a patient, according to an example.

Referring now to FIG. 7, a flowchart for a process 700 for applying cryotherapy to a target tissue in a nasal cavity of a patient is shown according to an example. As shown in FIG. 7, at block 710, the process 700 includes inserting a cryotherapy device into the nasal cavity of the patient. The cryotherapy device includes a cryotherapy delivery member. At block 712, the process 700 includes positioning the cryotherapy delivery member at a position that is proximate to an anterior ethmoidal nerve (AEN). At block 714, the process 700 includes delivering, using the cryotherapy delivery member, thermal energy to the AEN.

Figure 8:
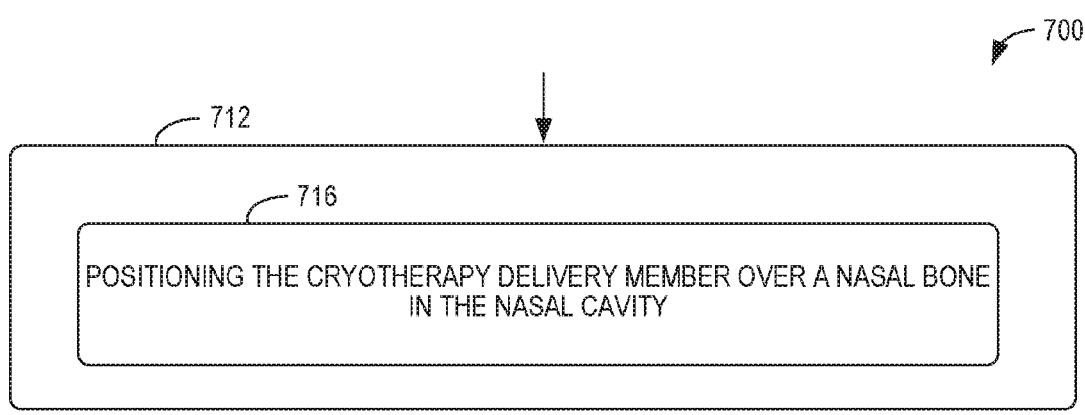
FIG. 8 illustrates a flowchart for a process for applying cryotherapy to a target tissue in a nasal cavity of a patient that can be used with the process shown in FIG. 7, according to an example.

FIGS. 8-15 depict additional aspects of the process 700 according to further examples. As shown in FIG. 8, positioning the cryotherapy delivery member at the position that is proximate to the AEN at block 712 can include positioning the cryotherapy delivery member over a nasal bone in the nasal cavity at block 716.

Figure 9:
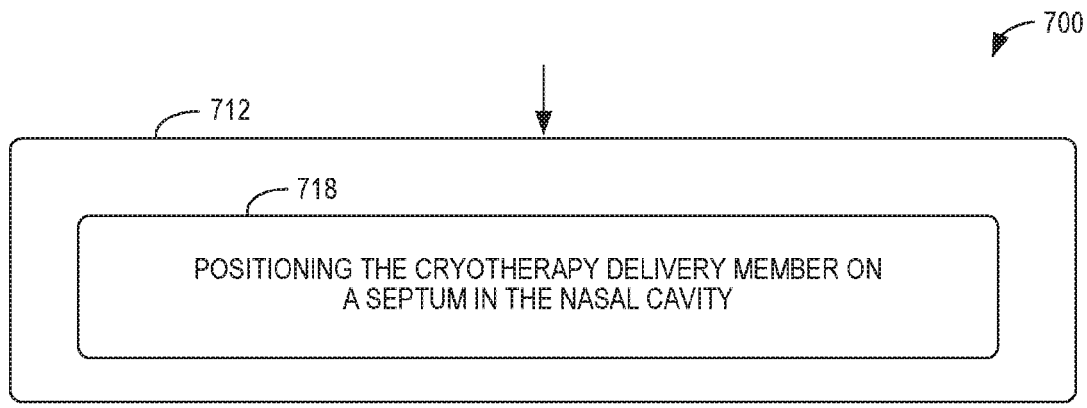
FIG. 9 illustrates a flowchart for a process for applying cryotherapy to a target tissue in a nasal cavity of a patient that can be used with the process shown in FIG. 7, according to an example.

As shown in FIG. 9, positioning the cryotherapy delivery member at the position that is proximate to the AEN at block 712 can include positioning the cryotherapy delivery member on a septum in the nasal cavity at block 718.

Figure 10:
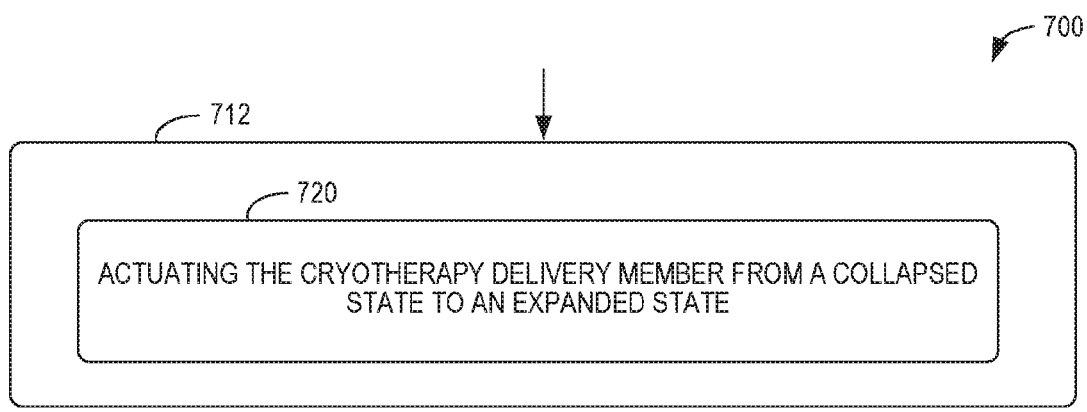
FIG. 10 illustrates a flowchart for a process for applying cryotherapy to a target tissue in a nasal cavity of a patient that can be used with the process shown in FIG. 7, according to an example.

As shown in in FIG. 10, positioning the cryotherapy delivery member at the position that is proximate to the AEN at block 712 can include actuating the cryotherapy delivery member from a collapsed state to an expanded state at block 720. In this example, the cryotherapy delivery member has a first size in the collapsed state, the cryotherapy delivery member has a second size in the expanded state, and the first size is smaller than the collapsed state.

Figure 11:
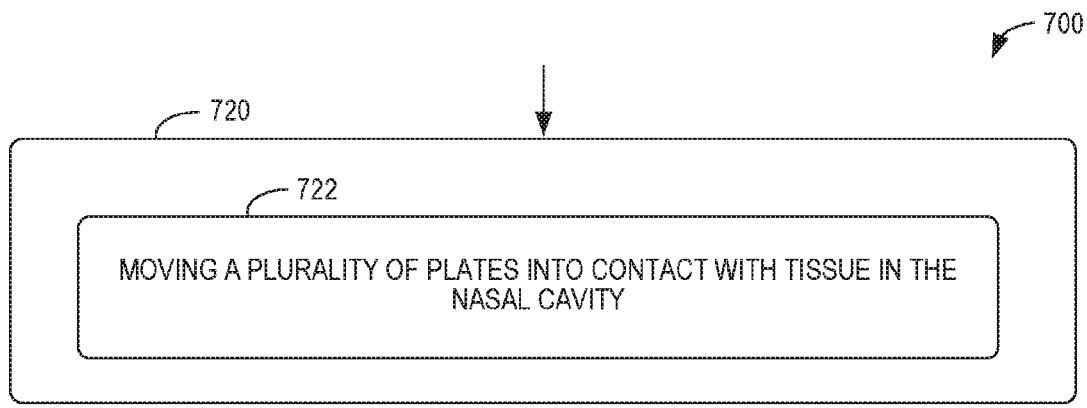
FIG. 11 illustrates a flowchart for a process for applying cryotherapy to a target tissue in a nasal cavity of a patient that can be used with the process shown in FIG. 10, according to an example.

As shown in FIG. 11, actuating the cryotherapy delivery member at block 720 can include moving a plurality of plates into contact with tissue in the nasal cavity at block 722.

Figure 12:
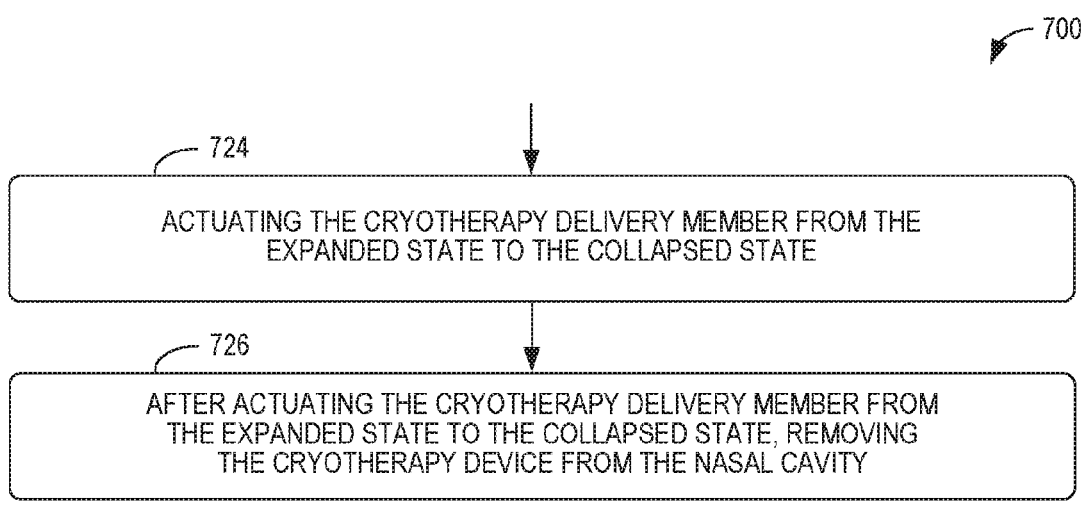
FIG. 12 illustrates a flowchart for a process for applying cryotherapy to a target tissue in a nasal cavity of a patient that can be used with the process shown in FIG. 10, according to an example.

As shown in FIG. 12, the process 700 can further include actuating the cryotherapy delivery member from the expanded state to the collapsed state at block 724 and, after actuating the cryotherapy delivery member from the expanded state to the collapsed state at block 724, removing the cryotherapy device from the nasal cavity at block 726.

Figure 13:
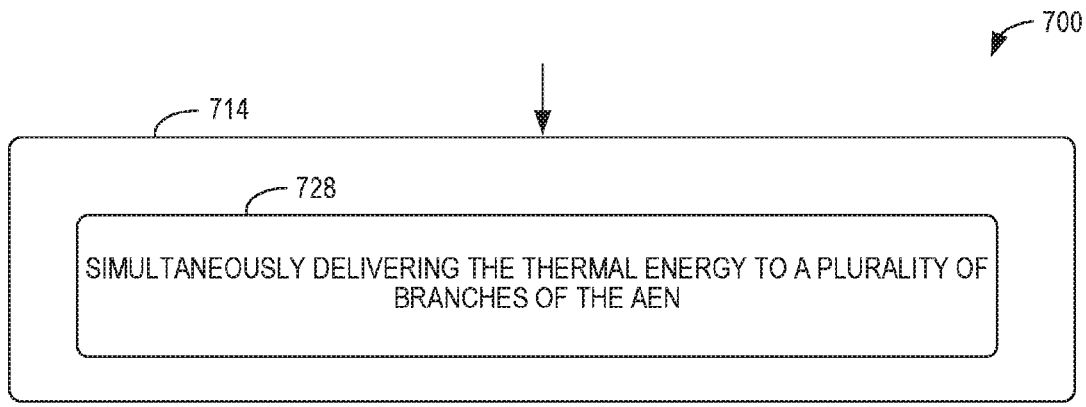
FIG. 13 illustrates a flowchart for a process for applying cryotherapy to a target tissue in a nasal cavity of a patient that can be used with the process shown in FIG. 7, according to an example.

As shown in FIG. 13, delivering the thermal energy to the AEN at block 714 can include simultaneously delivering the thermal energy to a plurality of branches of the AEN at block 728.

Figure 14:
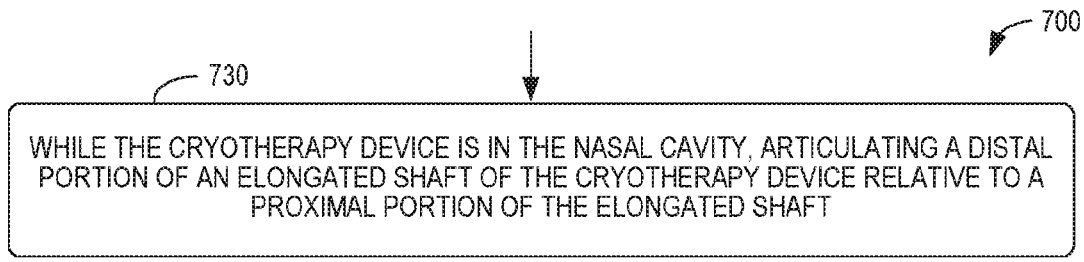
FIG. 14 illustrates a flowchart for a process for applying cryotherapy to a target tissue in a nasal cavity of a patient that can be used with the process shown in FIG. 7, according to an example.

As shown in FIG. 14, the process 700 can include, while the cryotherapy device is in the nasal cavity, articulating a distal portion of an elongated shaft of the cryotherapy device relative to a proximal portion of the elongated shaft at block 730.

Figure 15:
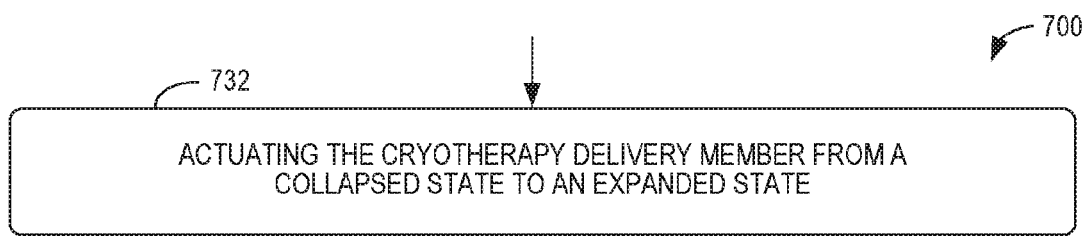
FIG. 15 illustrates a flowchart for a process for applying cryotherapy to a target tissue in a nasal cavity of a patient that can be used with the process shown in FIG. 7, according to an example.

As shown in FIG. 15, the process 700 can also include actuating the cryotherapy delivery member from a collapsed state to an expanded state at block 732.

Though the disclosures presently-disclosed have primarily been discussed in the context of cryotherapy, the devices, systems, and methods described can have applicability with other ablative and non-ablative surgical techniques. For example, embodiments can include devices, systems, and methods that utilize heating/hyperthermia therapies. Embodiments utilizing heating/hyperthermia therapies can be similar in structure and steps as embodiments utilizing hypothermic therapies. Sources of heat for use with hyperthermia-based therapies can include radiofrequency (RF) energy, microwave energy, ultrasound energy, resistive heating, exothermic chemical reactions, combinations thereof and other heat sources known to those skilled in the art. Further, the disclosure can be applied as a standalone system or method, or as part of an integrated medical treatment system. It shall be understood that different aspects of the disclosure can be appreciated individually, collectively, or in combination with each other.

The methods described herein can be utilized effectively with any of the embodiments or variations of the devices and systems described above, as well as with other embodiments and variations not described explicitly in this document. The features of any of the systems or system components described in any of the embodiments herein can be used in any other suitable embodiment of a system or system component.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A cryotherapy device, comprising:
   an elongated shaft; and
   a cryotherapy delivery member coupled to a distal end of the elongated shaft, wherein the cryotherapy delivery member comprises a plurality of plates and a plurality of rods coupling the plurality of plates to the distal end of the elongated shaft,
   wherein the cryotherapy delivery member is configured to apply, from a fixed position in a nasal cavity, by one or more of the plurality of plates contacting a nasal wall, cryotherapy to at least one nerve in the nasal cavity or at least one branch of a nerve in the nasal cavity.

2. The cryotherapy device of claim 1, wherein the cryotherapy delivery member is actuatable between (i) a collapsed state and (ii) an expanded state,
   wherein the cryotherapy delivery member has a first size in the collapsed state,
   wherein the cryotherapy delivery member has a second size in the expanded state, and
   wherein the first size is smaller than the second size.

3. The cryotherapy device of claim 2, wherein
   the plurality of rods couple the plurality of plates to an adjustable pivot point at the distal end of the elongated shaft.

4. The cryotherapy device of claim 3, wherein the plurality of rods and the adjustable pivot point are configured to adjust at least one of a position, a distance, or an angle of the plurality of plates relative to each other.

5. The cryotherapy device of claim 3, wherein the plurality of plates are actuatable independently of each other to selectively apply cryotherapy using a subset of the plurality of plates.

6. A cryotherapy device comprising:
   an elongated shaft; and
   a cryotherapy delivery member coupled to a distal end of the elongated shaft, wherein the cryotherapy delivery member comprises:
      a first cryotherapy delivery member configured to apply cryotherapy to a first nerve in a nasal cavity or a first branch of a nerve in the nasal cavity, and
      a second cryotherapy delivery member configured to apply cryotherapy to a second nerve in the nasal cavity or a second branch of the nerve in the nasal cavity,
      wherein the first cryotherapy delivery member and the second cryotherapy delivery member are configured to be inserted into one nostril of the nasal cavity and are configured to be articulated independently relative to each other.

7. The cryotherapy device of claim 6, wherein the elongated shaft is bifurcated into a first section and a second section,
   wherein the first cryotherapy delivery member is coupled to the first section of the elongated shaft, and
   wherein the second cryotherapy delivery member is coupled to the second section of the elongated shaft.

8. The cryotherapy device of claim 7, wherein the first section of the elongated shaft is configured to position the first cryotherapy delivery member at a posterior region of the nasal cavity, and
   wherein the second section of the elongated shaft is configured to position the second cryotherapy delivery member at an antero-superior region of the nasal cavity.

9. The cryotherapy device of claim 6, wherein the first cryotherapy delivery member and the second cryotherapy delivery member are actuatable independently of each other to selectively apply cryotherapy using only one of the first cryotherapy delivery member and the second cryotherapy delivery member.

10. The cryotherapy device of claim 6, wherein the first cryotherapy delivery member and the second cryotherapy delivery member are actuatable at the same time to simultaneously apply cryotherapy using both of the first cryotherapy delivery member and the second cryotherapy delivery member.

11. The cryotherapy device of claim 6, further comprising:
   a stabilization feature coupled to the first cryotherapy delivery member to maintain a position of the first cryotherapy delivery member while positioning the second cryotherapy delivery member.

12. The cryotherapy device of claim 11, wherein the stabilization feature comprises vacuum suction.

* * * * *